United States Patent [19]

Murib et al.

[11] Patent Number: 5,072,005
[45] Date of Patent: Dec. 10, 1991

[54] PROCESS FOR THE PREPARATION OF METHYL 4-OXOBUTYRATE AND ITS METHANOL ADDITION PRODUCTS

[75] Inventors: Jawad H. Murib, Cincinnati; William D. Baugh, Wilmington, both of Ohio

[73] Assignee: National Distillers and Chemical Corporation, New York, N.Y.

[21] Appl. No.: 71,452

[22] Filed: Jul. 9, 1987

Related U.S. Application Data

[63] Continuation-in-part of Ser. No. 902,902, Sep. 2, 1986, abandoned, which is a continuation of Ser. No. 777,391, Sep. 14, 1985, abandoned, which is a continuation of Ser. No. 264,925, May 18, 1981, abandoned.

[51] Int. Cl.$^5$ .................... C07D 307/32; C07D 67/36; C07D 69/66
[52] U.S. Cl. .................... 549/313; 560/175; 560/186
[58] Field of Search .................... 560/175, 186; 260/410.9; 549/313

[56] References Cited

U.S. PATENT DOCUMENTS 3,818,060  6/1974  Forster .................... 260/413

FOREIGN PATENT DOCUMENTS 2124718  12/1981  Fed. Rep. of Germany ...... 562/522
1123367   8/1968  United Kingdom ............ 560/233

Primary Examiner—Jose G. Dees
Attorney, Agent, or Firm—Kenneth D. Tremain; Gerald A. Baracka

[57] ABSTRACT

Methyl 4-oxobutyrate and its methanol addition products, methyl 4,4-dimethoxybutyrate and gamma-methoxy-gamma-butyrolactone, which are useful as intermediates in the preparation of such industrially important compounds as gamma-butyrolactone, 1,4-butanediol and glutamic acid, are produced from the reaction of acrolein, carbon monoxide and methanol in the presence of a catalyst system which consists of (a) a Group VIII metal component selected from palladium metal or a palladium-containing composition which generates palladium metal under reaction conditions, (b) a hydrogen halide and (c) an arylarsine catalyst copromoter.

14 Claims, No Drawings

PROCESS FOR THE PREPARATION OF METHYL 4-OXOBUTYRATE AND ITS METHANOL ADDITION PRODUCTS

This is a continuation-in-part of copending U.S. application Ser. No. 902,902, filed on Sept. 2, 1986, abandoned, which in turn is a continuation of U.S. application Ser. No. 777,391, filed on Sept. 14, 1985, now abandoned, which is in turn a continuation of U.S. application Ser. No. 264,925, filed on May 18, 1981, now abandoned.

BACKGROUND OF THE INVENTION

This invention relates to a process for making esters and, more particularly, to methyl 4-oxobutyrate and its methanol addition products, viz., methyl 4,4-dimethoxybutyrate and gamma-methoxy-gamma-butyrolactone, from the catalyzed reaction of acrolein, carbon monoxide and methanol. Methyl 4-oxobutyrate is a useful intermediate in the production of a variety of industrially useful compounds including gamma-butyrolactone, 1,4-butanediol and glutamic acid.

U.S. Pat. No. 3,382,274 to Fenton describes the reaction of an aliphatic, alpha, beta-ethylenically unsaturated aldehyde such as acrolein with an aliphatic or alicyclic primary alcohol such as methanol in the presence of mercuric ion to yield an ester of a beta-alkoxy aliphatic carboxylic acid. U.S. Pat. No. 3,397,225 to Fenton, et al. describes the oxidative carbonylation of an olefin, carbon monoxide and alkanol in the presence of a platinum group metal and a soluble salt of a multivalent metal as an oxidant having an oxidation potential more positive than the platinum group metal to provide the ester of an alpha, beta-unsaturated carboxylic acid having one more carbon than the starting olefin. In a somewhat similar process, that of U.S. Pat. No. 3,437,676 to von Kutepow, et al., a carbonylation reaction is carried out in which olefin, carbon monoxide and alcohol are reacted in the presence of a catalyst such as palladium dichloride bis(triphenylphosphine) to provide a carboxylic acid ester. U.S. Pat. No. 4,245,115 to Butter describes a similar carbonylation employing, as catalyst, a palladium salt complexed with an arsine or stibine ligand, e.g., palladium dichloride bis (triphenylarsine) or palladium dichloride bis (tri-p-tolylarsine). The process of U.S. Pat. No. 3,980,697 to El-Chahawi, et al. provides beta-alkoxy-butyric acid alkyl esters by the reaction of allyl halides with carbon monoxide, alkali alcoholates and alcohols. U.S. Pat. No. 2,040,944 to Lazier and U.S. Pat. No. 2,091,800 to Adkins, et al. show that the reaction of an ester with hydrogen provides an alcohol. U.S. Pat. No. 3,065,243 to Dunlop, et al. describes the preparation of gamma-butyrolactone by the hydrogenation of the anhydrides or esters of succinic acid or maleic acid. Similarly, U.S. Pat. No. 3,113,138 to Franko-Filipasic, et al., U.S. Pat. No. 3,214,385 to Kolyer, U.S. Pat. No. 3,580,930 to Miya, et al. and U.S. Pat. No. 4,048,196 to Broecker, et al. each describes the preparation of gamma-butyrolactone by the hydrogenation of succinic anhydride.

SUMMARY OF THE INVENTION

It has not been discovered that methyl 4-oxobutyrate and its methanol addition products, i.e., methyl 4,4-dimethoxy-butyrate and gamma-methoxy-gamma-butyrolactone, can be readily and conveniently produced by the reaction of acrolein, carbon monoxide and methanol in the presence of a catalyst system comprising: (a) a Group VIII metal component selected from a palladium metal or a palladium-containing composition which provides palladium metal under reaction conditions, (b) hydrogen halide and (c) and an arylarsine. Methyl 4-oxobutyrate can be selectively hydrogenated to either gamma-butyrolactone (over Raney nickel, ruthenium or palladium on carbon, copper on zinc oxide, etc.) or 1,4-butanediol (over copper chromite). Gamma-butyrolactone is readily employed as a solvent for resins, in paint removers, and as an intermediate for the production of 1,4-butanediol, tetrahydrofuran, and succinic acid. 1,4-Butanediol is an important solvent and chemical intermediate for the manufacture of a host of organic compounds including pharmaceuticals and polyester and polyurethane resins.

DESCRIPTION OF THE PREFERRED EMBODIMENTS

The reaction of acrolein, carbon monoxide and methanol to provide methyl 4-oxobutyrate and its methanol addition products such as methyl 4,4-dimethoxybutyrate and gamma-methoxy-gamma-butyrolactone is carried out in the presence of a catalyst system which comprises (a) a Group VIII metal component selected from palladium metal or a palladium-containing composition which provides palladium metal under reaction conditions (b) a hydrogen halide and (c) an arylarsine co-promoter. Of the palladium components useful in the present process, palladium metal and palladium acetylacetonate are preferred, with palladium metal being most preferred. The palladium metal may be supported on an inert carrier such as alumina, silica, titania, zirconia, carbon, diatomaceous earth, glass beads, clay, ceramic, carborundum and the like. It is especially preferred that a supported palladium metal catalyst be employed, palladium metal supported on either alumina or carbon having demonstrated particularly good results.

The palladium metal may be incorporated on the support in amounts of from about 0.1 to about 8 percent, preferably from about 0.5 to about 5 percent, by weight of the total supported catalyst. If another metal is also present in the catalyst composition, it can be incorporated in an amount ranging from about 1 to about 500%, preferably from about 10 to about 200 percent by weight based on the weight of the palladium metal or other palladium containing compounds. The catalyst system contains hydrogen halide, preferably hydrogen chloride. The hydrogen halide is believed to act as a promoter in the process of this invention without being consumed since it is ultimately regenerated in situ. Furthermore, an arylarsine acting as a catalyst co-promoter is also used in order to further increase the reaction rate. The preferred co-promoters are triarylarsines with triphenylarsine and tritolylarsine being most preferred. The optimum quantities of catalyst and acid employed can be readily determined experimentally for a given quantity of acrolein, carbon monoxide and methanol and a given set of reaction conditions to achieve a desired reaction rate.

Without wishing to be bound, acrolein is believed to undergo reaction with methanol and hydrogen halide (illustrated for hydrogen chloride) to provide beta-chloro-propionaldehyde dimethyl acetal as follows:

$$CH_2=CHCHO + HCl + 2CH_3OH \rightarrow ClCH_2CH_2CH(OCH_3)_2 + H_2O \quad \text{(Eq.1)}$$

Carbonylation of the acetal and subsequent methanolysis to provide methyl 4,4-dimethoxybutyrate are thought to proceed as follows:

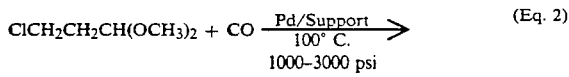

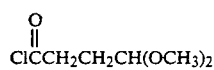

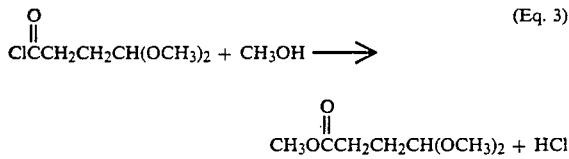

In place of acrolein, an acetal of acrolein, e.g., $CH_2=CHCH(OCH_3)_2$, can be used. Accordingly, the term "acrolein" herein shall be understood as referring to acrolein or acrolein acetal.

The reaction may proceed via carbonylation of beta-chloropropionaldehyde, formed by addition of HCl to acrolein:

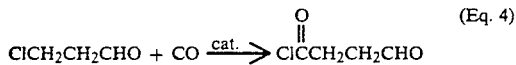

Methanolysis of the acyl chloride provides methyl 4-oxobutyrate:

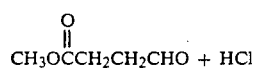

Further reaction with methanol gives the hemi acetal or dimethyl acetal. The hemi acetal can undergo cyclization to gamma-methoxy-gamma-butyrolactone with elimination of methanol as follows:

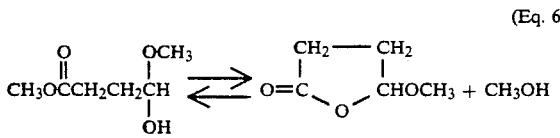

The reaction can be carried out in a flow-trickle phase, fixed bed or stirred reactor.

Conventional recovery techniques such as simple distillation can be used to separate the carbonylation products, hydrogen halides and unreacted methanol from the catalyst thus permitting convenient recycling of the catalyst residue.

Catalytic hydrogenation of methyl 4-oxobutyrate, methyl 4,4-dimethoxybutyrate and gamma-methoxy-gamma-butyrolactone in a second stage using a Group VIII or a Group IB metal will provide gamma-butyrolactone. More specifically, the catalytic hydrogenation of methyl 4-oxobutyrate, methyl 4,4-dimethoxybutyrate and γ-methoxy-γ-butyrolactone employing Raney nickel, ruthenium or palladium on carbon or copper on zinc oxide can be effected in the presence of water and an acid co-catalyst such as para-toluenesulfonic acid to form gamma-butyrolactone. The hydrogenation can also be carried out in the presence of copper chromite to provide 1,4-butanediol.

In a variation of the Strecker reaction described by Huffman, et al. *Chem. Rev.* 63, 625 (1963) in which the oxo products resulting from the reaction of methyl acrylate, hydrogen and carbon monoxide are treated with hydrogen cyanide to form the cyanohydrin, then with ammonia followed by hydrolysis to give glutamic acid, methyl 4-oxobutyrate obtained in accordance with the present invention can be simultaneously or sequentially reacted with hydrogen cyanide and ammonia followed by hydrolysis of the resulting amino-nitrile to provide glutamic acid which, in the form of its monosodium salt, is widely used as a food flavor enhancer.

The following examples are further illustrative of the process of the invention:

EXAMPLE 1

A 300 ml Hastelloy reactor was provided with a stirrer, a thermocouple and a dip tube for sample withdrawal. Into the reactor was placed a mixture of 5 g 5% palladium supported on carbon and 3 g triphenylarsine. The reactor was purged with $N_2$ and charged with a solution containing 29.2 g acrolein (97% purity), 50.1 g methanol and 1.7 g anhydrous hydrogen chloride. The reactor was pressurized with carbon monoxide to 2400 psi, sealed and heated at 99°-106° C. with stirring. A sample was withdrawn after 30 minutes reaction time and analyzed by gas chromatography coupled with mass spectrometry. The analyses showed the presence of methyl 4-oxobutyrate, methyl 4,4-dimethoxybutyrate and gamma-methoxy-gamma-butyrolactone. No branched isomers were detected in the reaction mixture. An aliquot of the above sample was analyzed for ester content (measure of carbonylation) by room temperature saponification after neutralization of free HCl at 0° C. The analysis indicated a yield of 56.9% of $C_4$ esters expressed as methyl 4-oxobutyrate. Analyses of an additional sample taken after one hour of reaction time indicated a yield of 76.1% of methyl 4-oxobutyrate based on initial charge of acrolein.

EXAMPLE 2

A solution of 8.6 g acrolein dimethyl acetal and 0.9 g anhydrous hydrogen chloride in 7.9 g methanol was placed in a 70 ml Hastelloy pressure reactor containing 0.5 g of 5% palladium supported on alumina and 0.6 g of triphenylarsine. The reactor was pressurized with carbon monoxide to 3500 psi, sealed and shaken at 90° C. for ten hours. The reactor was cooled, the contents filtered and the filtrate was subjected to flash distillation in vacuo condensing the volatile materials at −80° C. Both proton and carbon-13 NMR analysis of the −80° condensate showed the product to be methyl 4,4-dimethoxybutyrate with not evidence of branched isomers. Area peak integration of the proton distribution gave the following ratios:

|  | CH$_3$OC (O) | (alpha) CH$_2$ | (beta) CH$_2$ | (Acetal) CH | (OCH$_3$)$_3$ |
| --- | --- | --- | --- | --- | --- |
| Calculated for CH$_3$OCCH$_2$CH$_2$CH(OCH$_3$)$_2$ (O) | 3 | 2 | 2 | 1 | 6 |
| Observed | 3.2 | 2.1 | 2 | 1 | 6.3 |

The observed ratios and chemical shift data are in good agreement with the structure.

EXAMPLE 3

The −80° C. condensate obtained in Example 2 was neutralized to pH 7 with aqueous sodium hydroxide at 0° C. and the product extracted with ether. After evaporation of the ether, the extract was treated with 2 ml of water and analyzed by GC which showed the presence of methyl 4-oxobutyrate, methyl 4,4-dimethoxybutyrate, and gamma-methoxy-gamma-butyrolactone. This mixture was hydrogenated in the presence of 0.17 g 5% ruthenium/carbon and a trace of p-toluenesulfonic acid at 100° C. and 1000 psi of H$_2$ for ten hours. The hydrogenated mixture was cooled to room temperature and filtered. The filtrate was analyzed by GC-mass spectrometry and NMR. The GC analysis showed disappearance of methyl 4-oxobutyrate, methyl 4,4-dimethoxy-butyrate and gamma-methoxy-gamma-butyrolactone with formation of gamma-butyrolactone and a small amount of its precursor, methyl 4-hydroxybutyrate, HOCH$_2$CH$_2$CH$_2$COOCH$_3$. The carbon-13 NMR analysis confirmed the presence of gamma-butyrolactone and methyl 4-hydroxybutyrate, HOCH$_2$CH$_2$CH$_2$COOCH$_3$ as the hydrogenation products. The observed C-13 chemical shifts for the C$_4$ hydroxy ester listed below are compared with the calculated values based on the C-13 chemical shifts of methyl butyrate and the well characterized substituent effects for the -OH group.

|  | (beta) HOCH$_2$ CH$_2$ | (alpha) CH$_2$ | C (O) | OCH$_3$ |
| --- | --- | --- | --- | --- |
| Calculated for HOCH$_2$CH$_2$CH$_2$COCH$_3$ (O) | 61.6 28.8 | 30 | 174.7 | 52 |
| Observed | 61.6 28.1 | 30.7 | 175.1 | 51.8 |

The excellent agreement between observed and calculated values clearly confirms the HOCH$_2$Ch$_2$CH$_2$COOCH$_3$ structure. These observations indicate that catalytic hydrogenation of the carbonylation products gives methyl 4-hydroxybutyrate as an intermediate which, upon distillation, eliminates methanol with the formation of gamma-butyrolactone.

EXAMPLE 4

Example 1 was repeated except that 10 g of water were added to the reaction mixture. After two hours of reaction time, ester determination indicated formation of methyl 4-oxobutyrate in 77.5% yield based on initial charge of acrolein.

EXAMPLE 5

A solution of 3.5 g anhydrous hydrogen chloride dissolved in 23.8 g of methanol was added dropwise to a stirred solution of 36.7 g acrolein dissolved in 43.7 g methanol maintained at 35°–40° C. A sample, 18.8 g, of the above solution was placed in a 70 ml Hastelloy pressure reactor containing 0.5 g of 5 wt. % palladium supported on carbon and 0.6 g of triphenylarsine. The reactor was pressurized with carbon monoxide at 3500 psi, sealed and shaken in a heated oven at 100° C. for six hours. After cooling, the reaction mixture was filtered and analyzed by gas chromatography. The analysis indicated complete conversion of the acrolein with formation of methyl 4-oxobutyrate in admixture with its methanol addition products. Only 1.8% of the initial acrolein underwent side reaction to give non-volatile residue.

EXAMPLE 6

Example 1 was repeated except that the HCl content was decreased to 0.2 g and the reaction was carried out at 1350 psi of carbon monoxide and 133° C. for six hours. Ester determination showed that 26.3% of the acrolein was converted to methyl 4-oxobutyrate.

EXAMPLE 7

The procedure of Example 1 was repeated using 70 ml methanol solution containing 22.9 g acrolein, 39.8 g methanol, 1.75 g of 5% Pd/C, 2.2 g HCl and 2.17 g triphenylarsine. The reaction was carried out at 115° C. and initial carbon monoxide pressure of 2700 psi. After one hour, ester determination indicated formation of 24.9 g of C$_4$ esters expressed as methyl 4-oxobutyrate amounting to a production rate of 285 g/g Pd/hr.

EXAMPLE 8

Example 1 was repeated without triphenylarsine. After a reaction time of one hour, the yield of methyl 4-oxobutyrate was 27.4%. At two hours the yield increased to 36.6% based on initial charge of acrolein.

The efficacy of arylarsines as co-promoters relative to arylphosphines, as well as arylstibines and arylbismuthines is demonstrated in the following experiments:

EXAMPLE 9

A 70 ml Hastelloy Parr reactor provided with a glass liner and a magnetic stirrer was used. The liner was flushed with nitrogen and charged with 9.6 g methanol containing 0.6 g anhydrous hydrogen chloride, 0.65 g triphenylarsine and 0.5 g of 5% palladium supported on alumina. The charged liner was then cooled in an ice bath amd 4.3 g of acrolein were added slowly while stirring. After removal of the magnetic stirrer, the liner was placed in the reactor which was flushed twice with carbon monoxide and pressurized with carbon monoxide at 3500 psi at room temperature and sealed. The sealed reactor was shaken in a heated air oven at 100° C. for 6 hours. Upon cooling to room temperature, the reactor was vented slowly, opened and the clear pale yellow reaction solution was filtered and the filtrate analyzed by gas chromatography. The results are shown in Table I.

EXAMPLE 10

The procedure of Example 9 was repeated except 0.73 g tri-p-tolylarsine was substituted for triphenylarsine. As in Example 9, the reaction product was a clear pale yellow solution. The results are shown in Table I.

EXAMPLE 11

The procedure of Example 9 was repeated except that 0.55 g triphenylphosphine was substituted for triphenylarsine. The results are indicated in Table I. Besides the products shown in Table I, a dark brown viscous non-volatile material was also isolated.

EXAMPLE 12

The procedure of Example 9 was repeated except that 0.92 g triphenylbismuthine was substituted for triphenylarsine. The results are shown in Table I. Besides the products shown in Table I, a dark brown viscous, non-volatile material was also isolated.

EXAMPLE 13

The procedure of Example 9 was repeated except that 0.74 g triphenylstibine was substituted for triphenylarsine. The results are shown in Table I. Besides the products shown in Table I, a dark brown, viscous, non-volatile material was also isolated.

TABLE I

| | EFFECT OF DIFFERENT LIGANDS | | | |
|---|---|---|---|---|
| | | Relative Composition of Products[1] | | |
| Example | Ligand | Methyl 4-Oxo-butyrate | Methyl 4,4-Dimethoxy-butyrate | gamma-Methoxy-gamma-Butyro-lactone |
| 9 | AsPh$_3$ | 28.8 | 24.9 | 10.8 |
| 10 | As(p-PhCH$_3$)$_3$ | 26.4 | 25.4 | 9.2 |
| 11 | PPh$_3$ | 11.0 | 4.5 | 2.5 |
| 12 | BiPh$_3$ | 3.2 | 0.2 | 2.2 |
| 13 | SbPh$_3$ | 2.7 | 0.6 | 3.2 |

[1] By GC area %, balance unconverted acrolein and methanol.

As shown by the results obtained in Examples 9–13, triarylarsines such as triphenylarsine and tritolylarsine are surprisingly more efficient than either triphenylphosphine, triphenylbismuthine or triphenylstibine as co-promoters in the carbonylation of acrolein. In Examples 11, 12 and 13 described hereinabove, the acrolein samples that were carbonylated in the presence of triphenylphosphine, triphenylbismuthine and triphenylstibine became very dark and viscous and gave very little yields of carbonylation products. The formation of the viscous products in Examples 11–13 further confirms that acrolein polymerizes not only in the presence of triphenylphosphine as described in *Acrolein*, edited by C. W. Smith, p. 230 (1962), but that acrolein also polymerizes in the presence of triphenylbismuthine and triphenylstibine. The acrolein samples that were carbonylated in the presence of triphenylarsine and tritolylarsine turned yellow and gave a good carbonylation product with little or no formation of polymerization products.

EXAMPLE 14

The procedure of Example 9 was repeated using 0.05 g palladium acetylacetonate (Pd(acac)$_2$), 0.4 g triphenylarsine, 8 g methanol containing 0.2 g anhydrous HCl and 4.3 g acrolein. The bomb was heated at 90° C. at 3500 psi CO with shaking for one hour. Palladium metal was produced in situ as evidenced by the presence of a palladium mirror on the reactor wall. Ester determination showed formation of methyl 4-oxobutyrate in 68.8% yield based on initial charge of acrolein.

What is claimed is:

1. A process for preparing at least one compound selected from methyl 4-oxobutyrate, methyl 4,4-dimethoxy-butyrate and γ-methoxy-γ-butyrolactone which comprises reacting acrolein, carbon monoxide and methanol in the presence of a three-component catalyst system, comprising (a) a Group VIII metal component selected from palladium metal or a palladium-containing composition which generates palladium metal under reaction conditions, (b) a hydrogen halide and (c) an arylarsine catalyst co-promoter.

2. The process of claim 1 wherein the Group VIII metal component is palladium metal or palladium acetylacetonate.

3. The process of claim 2 wherein the Group VIII metal component is palladium metal.

4. The process of claim 3 wherein the palladium metal is supported on an inert carrier.

5. The process of claim 4 wherein the inert carrier is alumina or carbon.

6. The process of claim 1 wherein the catalyst co-promoter is triarylarsine.

7. The process of claim 6 wherein the triarylarsine is triphenylarsine or tritolylarsine.

8. The process of claim 1 wherein the hydrogen halide is hydrogen chloride.

9. The process of claim 1 wherein the acrolein, carbon monoxide and methanol are heated at a temperature within the range of from about 90° C. to about 135° C. under a pressure of from about 1350 to about 3500 psi.

10. The process of claim 4 wherein the palladium metal is incorporated in amounts of from about 0.1 to about 8 percent based upon the weight of the total supported catalyst.

11. The process of claim 10 wherein the palladium metal is incorporated in amounts of from 0.5 to about 5 percent based upon the weight of the total supported catalyst.

12. The process according to claim 1 wherein at least one compound selected from methyl 4-oxobutyrate, methyl 4,4-dimethoxybutyrate and γ-methoxy-γ-butyrolactone is prepared by reacting acrolein, carbon monoxide and methanol in the presence of palladium metal supported on an inert carrier, hydrogen chloride and a triarylarsine catalyst co-promoter at a temperature in the range of from about 90° C. to about 135° C. and at a pressure of from about 1350 psi to about 3500 psi.

13. The process of claim 12 wherein the inert carrier is alumina or carbon.

14. The process of claim 12 wherein the triarylarsine is selected from triphenylarsine or tritolylarsine.

* * * * *